United States Patent
Colbaugh et al.

(10) Patent No.: US 11,707,595 B2
(45) Date of Patent: Jul. 25, 2023

(54) CONTROLLING LIGHT EXPOSURE FOR CIRCADIAN PHASE MANAGEMENT

(71) Applicant: KONINKLIJKE PHILIPS N.V., Eindhoven (NL)

(72) Inventors: Michael Edward Colbaugh, Level Green, PA (US); Mark Anthony Bartolomeo, Pittsburgh, PA (US); Stefanida Kononov Blake, Winchester, MA (US); Surya Subrahmanya Sreeram Vissapragada Venkata Satya, Monroeville, PA (US); Andreas Ralph Maihoefer, Pittsburgh, PA (US); Xia Chen, Lorton, VA (US); Boomika Kalyan, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 168 days.

(21) Appl. No.: 16/580,112

(22) Filed: Sep. 24, 2019

(65) Prior Publication Data
US 2020/0094015 A1    Mar. 26, 2020

Related U.S. Application Data

(60) Provisional application No. 62/736,038, filed on Sep. 25, 2018.

(51) Int. Cl.
| | | |
|---|---|---|
| *A61M 21/02* | (2006.01) | |
| *A61N 5/06* | (2006.01) | |
| *A61M 21/00* | (2006.01) | |

(52) U.S. Cl.
CPC .......... *A61M 21/02* (2013.01); *A61N 5/0613* (2013.01); *A61N 5/0618* (2013.01);
(Continued)

(58) Field of Classification Search
CPC .......... A61M 21/02; A61M 2021/0044; A61M 2205/502; A61M 2210/0612;
(Continued)

(56) References Cited

U.S. PATENT DOCUMENTS

| | | |
|---|---|---|
| 5,304,212 A | 4/1994 | Czeisler et al. |
| 7,520,607 B2 | 4/2009 | Casper et al. |

(Continued)

FOREIGN PATENT DOCUMENTS

| | | |
|---|---|---|
| CN | 101595421 A | 12/2009 |
| CN | 202892606 U | 4/2013 |

(Continued)

OTHER PUBLICATIONS

Chew, I. et al., "Smart lighting: The way forward? Reviewing the past to shape the future", Energy Building, 2017.

(Continued)

*Primary Examiner* — Sunita Reddy (57) ABSTRACT

This disclosure pertains to a system configured to control light exposure for circadian phase management and/or light deficient disorders of a subject. The system comprises a user interface, physiological sensors configured to generate output signals conveying physiological data of the subject, and a light control valve configured to block or reduce blue light ambient radiation reaching eyes of the subject. Processors are in communication with the user interface, the physiological sensors, the light control valve, and radiation generators. The processors cause the system to receive physiological goals of the subject, determine a light control plan based on the physiological goals, the physiological data, environmental data, and time data. The system operates the light control valve to block or reduce blue light ambient radiation based on the light control plan, and generate, using
(Continued)

the one or more radiation generators, therapeutic light radiation based on the light control plan.

24 Claims, 6 Drawing Sheets

(52) U.S. Cl.
CPC ............... *A61M 2021/0044* (2013.01); *A61M 2205/502* (2013.01); *A61M 2210/0612* (2013.01); *A61N 2005/0626* (2013.01); *A61N 2005/0663* (2013.01)

(58) Field of Classification Search
CPC .......... A61M 2230/04; A61M 2230/18; A61M 2230/30; A61M 2230/40; A61M 2230/50; A61M 2230/63; A61N 5/0613; A61N 5/0618; A61N 2005/0626; A61N 2005/0663; A61N 2005/0648; G16H 20/40
USPC ...................................... 600/26–28
See application file for complete search history.

(56) References Cited

U.S. PATENT DOCUMENTS

| | | | |
|---|---|---|---|
| 7,556,376 | B2 | 7/2009 | Ishak et al. |
| 7,748,845 | B2 | 7/2010 | Casper et al. |
| 7,770,666 | B2 | 8/2010 | Allen |
| 8,870,740 | B2 | 10/2014 | Clegg et al. |
| 9,094,231 | B2 | 7/2015 | Yoshida et al. |
| 9,374,876 | B2 | 6/2016 | Alpert et al. |
| 2010/0174345 | A1 | 7/2010 | Ashdown |
| 2012/0199995 | A1 | 8/2012 | Pugh et al. |
| 2012/0206050 | A1* | 8/2012 | Spero ...................... F21V 19/02 315/152 |
| 2012/0209358 | A1 | 8/2012 | Feng |
| 2016/0158486 | A1* | 6/2016 | Colbaugh ............ A61N 5/0618 607/88 |
| 2016/0166851 | A1* | 6/2016 | Pugh ...................... A61B 5/165 607/88 |
| 2016/0193442 | A1* | 7/2016 | Adamczyk ............ A61M 21/02 600/27 |
| 2016/0217672 | A1* | 7/2016 | Yoon ..................... A61B 5/4818 |
| 2016/0235940 | A1* | 8/2016 | Koifman ................ A61F 9/04 |
| 2017/0105265 | A1* | 4/2017 | Sadwick ................ H05B 47/11 |
| 2018/0339127 | A1* | 11/2018 | Van Reen ............ A61N 5/0618 |
| 2019/0209806 | A1* | 7/2019 | Allen ..................... G16H 20/70 |
| 2019/0290882 | A1* | 9/2019 | Chao ........................ A61B 5/11 |
| 2019/0366032 | A1* | 12/2019 | Lockley ................ A61M 21/02 |
| 2021/0275773 | A1* | 9/2021 | Albala ................ F21V 23/0471 |

FOREIGN PATENT DOCUMENTS

| | | |
|---|---|---|
| DE | 202014005928 U1 | 1/2015 |
| EP | 2778752 A2 | 9/2014 |
| KR | 2008040378 A | 5/2008 |
| KR | 201306766 U | 11/2013 |
| WO | 2009023968 A1 | 2/2009 |
| WO | 2009029575 A1 | 3/2009 |
| WO | 2015113003 A1 | 7/2015 |
| WO | 2016145064 A1 | 9/2016 |
| WO | 2017222997 A1 | 12/2017 |

OTHER PUBLICATIONS

Clip-on Blue Blocking Amber Lenses for Sleep - BioRhythm Safe(TM)—Nighttime Eye Wear—Special Orange Tinted Lenses Help You Sleep and Relax Your Eyes (Nighttime Lens), https://www.amazon.com/Clip-Blocking-Amber-Lenses-Sleep/dp/B071FPWQDX/ref-sr_1_1_a_it?ie=UTF8&qid=1505845926&sr=8-1&keywords=blue-blocking+glasses+clip+on, Accessed Sep. 20, 2019.
Österholm, A. et al., "Four Shades of Brown: Tuning of Electrochromic Polymer Blends Toward High-Contrast Eyewear", CS Applied Materials & Interfaces (vol. 7 issue 3 pp. 1413-1421 ) Jan. 28, 2015.
"goLITE BLU Engergy Light", Philips, https://www.usa.philips.com/c-p/HF3422_60/golite-blu-energy-light, Accessed Sep. 20, 2019.
Luminette 2—Worid's first Light Therapy Glasses, https://www.amazon.com/Luminette-Therapy-Glasses-Improve-Regulate/dp/B01553VBD6, Accessed Sep. 20, 2019.
Re-Timer Light Therapy Glasses, https://www.amazon.com/ReTimer-Light-Therapy-Glasses-Generation/dp/B01GGNOPAO/ref=cm_cr_arp_d_product_top?ie=UTF8, Accessed Sep. 20, 2019.

* cited by examiner

CONTROLLING LIGHT EXPOSURE FOR CIRCADIAN PHASE MANAGEMENT

CROSS-REFERENCE TO PRIOR APPLICATIONS

This application claims the benefit of U.S. Provisional Application No. 62/736,038, filed on 25 Sep. 2018. This application is hereby incorporated by reference herein.

BACKGROUND

1. Field

The present disclosure pertains to a system and method for controlling light exposure for circadian phase management.

2. Description of the Related Art

Commercial solutions for treating light deficient disorders and/or adjusting the phase of the human circadian system by controlling light exposure are known. Delivering light for photo-biological, therapeutic benefit and blocking blue-light using fixed filtering blue-blocking lens products and/or dynamic filtering characteristics is also known. Many commercial solutions fail to provide light delivery and blocking in a user friendly, accurate platform designed for controlling light exposure for a therapeutic benefit.

SUMMARY

Accordingly, one or more aspects of the present disclosure relate to a system configured to control light exposure for circadian phase management and/or light deficient disorders of a subject. In some embodiments, the system comprises a user interface, one or more physiological sensors configured to generate output signals conveying physiological data of the subject, and a light control valve configured to block or reduce blue light ambient radiation reaching eyes of the subject. In some embodiments, the system comprises one or more radiation generators configured to generate therapeutic light radiation onto the eyes of the subject. In some embodiments, the system comprises one or more processors in communication with the user interface, the one or more physiological sensors, the light control valve, and the one or more radiation generators. In some embodiments, the one or more processors cause the system to receive, via the user interface, physiological goals of the subject, determine a light control plan for the subject based on the physiological goals of the subject, the physiological data, environmental data, and time data. In some embodiments, the one or more processors are configured to operate the light control valve to block or reduce blue light ambient radiation based on the light control plan, and generate, using the one or more radiation generators, therapeutic light radiation based on the light control plan Another aspect of the present disclosure relates to a method for controlling light exposure for circadian phase management and/or light deficient disorders of a subject utilizing a light therapy system. The light therapy system comprises a user interface, one or more physiological sensors configured to generate output signals conveying physiological data of the subject, a light control valve configured to block or reduce blue light ambient radiation reaching eyes of the subject, one or more radiation generators configured to generate therapeutic light radiation onto the eyes of the subject, and/or other components. The light therapy system includes one or more processors in communication with the user interface, the one or more physiological sensors, the light control valve, and the one or more radiation generators. The method comprises receiving, via the user interface, physiological goals of the subject, determining a light control plan for the subject based on the physiological goals of the subject, the physiological data, environmental data, and time data, operating the light control valve to block or reduce blue light ambient radiation based on the light control plan, and generating, using the one or more radiation generators, therapeutic light radiation based on the light control plan.

Still another aspect of present disclosure relates to a device configured to control light exposure for circadian phase management and/or light deficient disorders of a subject. The device comprises means for receiving physiological goals of the subject and means for determining a light control plan for the subject based on the physiological goals of the subject, physiological data, environmental data, and time data. The device comprises means for operating a light control valve to block or reduce blue light ambient radiation based on the light control plan, and means for generating, using one or more radiation generators, therapeutic light radiation based on the light control plan.

These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly (i.e., through one or more intermediate parts or components, so long as a link occurs). As used herein, "directly coupled" means that two elements are directly in contact with each other. As used herein, "fixedly coupled" or "fixed" means that two components are coupled so as to move as one while maintaining a constant orientation relative to each other. As used herein, "operatively coupled" means that two elements are coupled in such a way that the two elements function together. It is to be understood that two elements "operatively coupled" does not require a direct connection or a permanent connection between them.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

In order to adjust the phase of the human circadian system, the specific characteristics and timing of light that a person experiences during the course of a day needs to be controlled appropriately. Some exemplary embodiments described herein include a device that a user wears all day, and can control the light entering the person's eyes, including but not limited to wavelengths that activate the non-visual tract of the optic nerve which are associated with controlling the body's circadian clock. Some exemplary embodiments may include one or more a non-wearable devices that can control the light entering the person's eyes, including but not limited to wavelengths that activate the non-visual tract of the optic nerve which are associated with controlling the body's circadian clock. Some embodiments described herein block counter-productive light from entering the eyes at some (e.g., "the wrong") times of the day, while allowing that same light to enter at other (e.g., "the right") times of the day. In some embodiments, the light controlling system and method described herein can produce light of various types of illumination to provide or supplement ambient light available in the ambient environment at predetermined (e.g., "key") times of the day.

The present system and method are configured to control or instruct a user about where/when/how to control the type of light they may need at any instant throughout the day; to maximize the progress towards a known set of physiological goals for an individual user. This process and proper use of light can help an individual adapt to shift-work, reduce the effect of jet lag, maximize drug efficacy, re-align their circadian phase to meet a desired sleep/wake schedule, or to reduce the symptoms of psychological disease or syndromes.

Some embodiments described herein help minimize the impact of real-world circadian phase related challenges such as shiftwork or jet lag by determining the configuration and use of light delivery and blocking components of the system (described below) as needed over minutes, hours, days, and/or weeks. In order to meet goals for circadian management and/or a photo-biological effect, some embodiments of the present system calculate, at any point in the day, what the exposure level to blue and other wavelengths of light should be for a subject, and control these in a device that a subject wears throughout the day and/or non-wearable devices configured to provide indoor light control.

Figure 1:
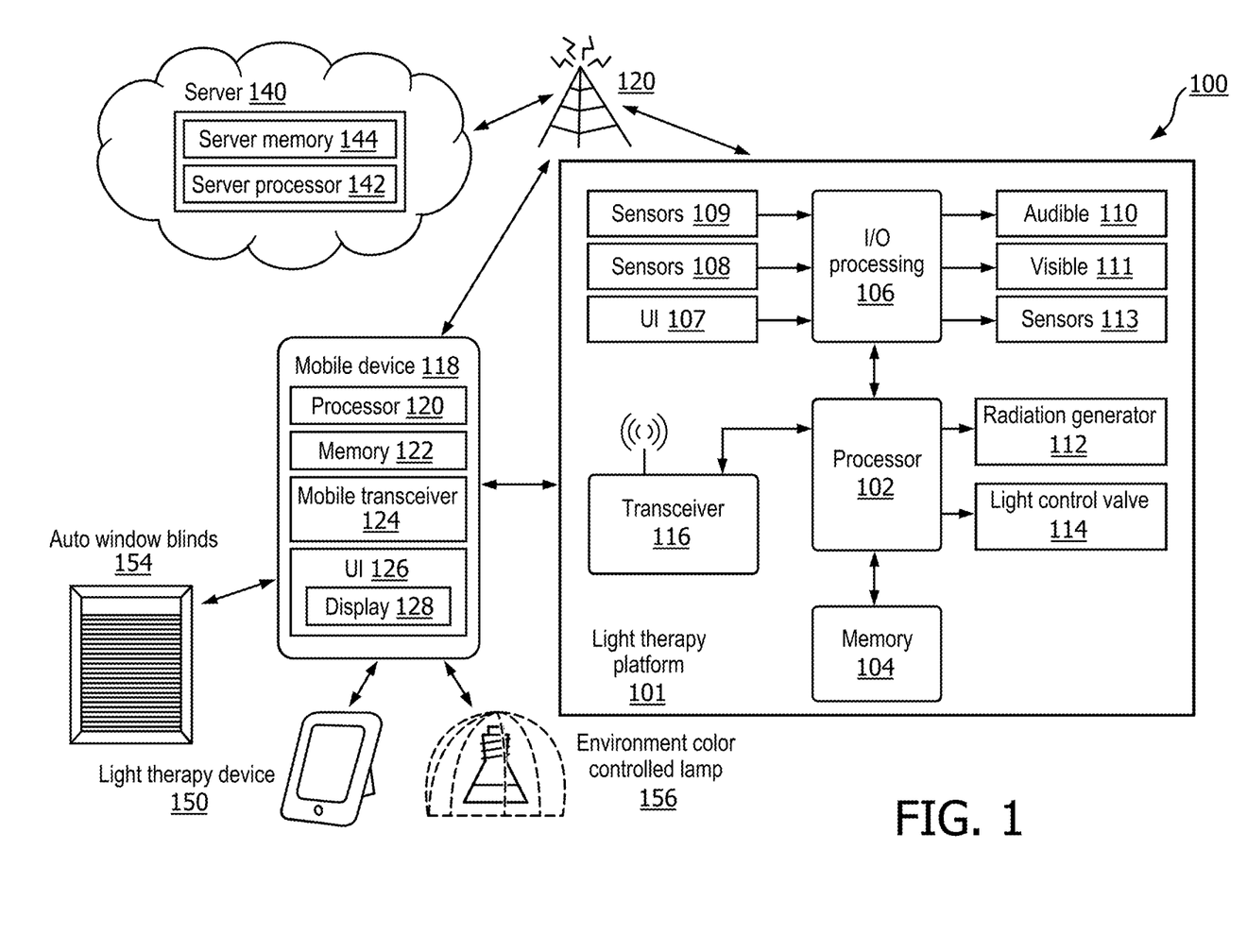
FIG. 1 is a schematic illustration of a light control system for controlling light exposure in accordance with one or more embodiments.

Referring now to FIG. 1, FIG. 1 depicts a schematic of the present light control system 100 configured to provide therapeutic light therapy to a subject. Light control system 100 may be configured to control light exposure for circadian phase management and/or light deficient disorders of a subject in accordance with a light control plan. In some embodiments, light control plan may determine at all points in the day what the subject's exposure of blue light and other wavelengths of light should be. Light control plan may be configured to block counter-productive light from entering the subject's eyes at some (e.g., "the wrong") times of the day, while allowing that same light to enter the subject's eyes at other (e.g., "the right") times of the day. In some embodiments, light control plan may include instructions corresponding to specific characteristics and timing of light radiation that the subject experiences during the course of one or more days. Specific characteristics and timing of light radiation may include light intensity level, wavelength, and duration, for example. In some embodiments, light control plan may be configured to administer light therapy based on the individual goals of the subject, which is discussed in further detail below.

In one embodiment, light control system 100 may include light therapy platform 101, mobile device 118, remote server 140, light therapy device 150, automated window blinds 154, environment color control lamp 156, and/or other components. In some embodiments, light therapy platform 101, mobile device 118, and remote server 140 may be configured to communicate with one another via network 120, for example. Network 120 may include a hybrid fiber optic long haul transmission network configured to provide an Internet connection. Network 120 may also include a local WAN/LAN network configured to provide local access to a HFC network for providing access to the Internet. In some embodiments, network 120 may include a wireless internet connection utilizing, for example, 3G, 4G, LTE, 5G, or other wireless carrier protocol.

As shown in FIG. 1, light therapy device 150, automated window blinds 154, and portable light therapy lamps 156 may be configured to communicate wirelessly (e.g., BLUETOOTH.TMIBLE.TM.) with mobile device 118 for implementing the light control plan in conjunction with light therapy platform 101. In some embodiments, components 150, 154, 156 may be directed to impacting circadian phase of the subject while indoors utilizing light therapy device 150, automated window blinds 154, environment color control lamps 156, and/or other environment automated illumination devices. By implementing non-wearable components 150, 154, 156, a user may switch light therapy utilizing the wearable device (i.e., light therapy platform 101) to the non-wearable devices (i.e., components 150, 154, 156). For example, in one embodiment, light therapy platform 101 and/or mobile device 118 may sense non-wearable components 150, 154, 156 as a subject comes within a predetermined physical proximity of components 150, 154, 156.

In some embodiments, automated window blinds 154 may include automated switchable window filters configured to filter blue light from the ambient environment. Window filters may include, but are not limited to, UV/IR/Blue blocking solar window films or surface shields, absorbent liquid coating, and/or polarized lenses. Light therapy device 150 may be configured to emit therapeutic light onto the eyes of a subject similar to radiation generators 112, discussed in further detail below. Environment color control lamp 156 may include a portable lamp that may be configured to emit ambient light of various wavelengths in accordance with the light control plan.

As shown in FIG. 1, remote servers 140 may include server processors 142, server memory 144, and/or other components. Remote servers 140 may be configured as a data center having one or more server racks configured as blade servers each having multiple processors and memory devices contained thereon. Remote servers 140 may be configured to access network 120 to communicate with mobile devices 118, and light therapy platform 101 for implementing the exemplary embodiments described herein. Server memory 144 may be configured as cloud memory via network 120 for providing virtual memory capabilities for light therapy platform 101, physical non-transitory memory, and/or other memory.

Light therapy platform 101 may be and/or be included in a garment and/or accessory (e.g., a pair of glasses or sunglass), and which is worn by the subject during the course of their normal activity, which is discussed in further detail below. In some embodiments, light control system 100 may include non-wearable components for providing light therapy, also discussed in further detail below. In some embodiments, non-wearable components may include light therapy device 150, automated window blinds 154, and/or environment color controlled lamp 156. Non-wearable components 150, 154, 156 may be utilized at a subjects residence, office, or any other building or structure suitable for controlling light exposure of the subject while indoors. For example, a building having automated window control, which can be controlled to allow certain bands of the light spectrum to be filtered-out, or to change the reflectivity or transmission properties of a window. In some embodiments, automated window control may include electro-active windows technologies such as electro-chromic and/or other liquid crystal window types.

As shown in FIG. 1, light therapy platform 101 may include processor 102, memory 104, I/O processing circuitry 106, platform user interface (UI) 107, physiological sensors 108, location sensors 109, environmental sensors 113, audible output 110, visual indicators 111, radiation generators 112, light control valves 114, transceiver 116, and/or other components. As further shown in FIG. 1, processor 102 may be in communication with memory 104, I/O processing circuitry 106, radiation generators 112, light control valves 114, transceiver 116, and/or other components that may be coordinated and controlled to consistently impact circadian phase.

Processor 102 may be configured to provide information processing and/or system control capabilities in light therapy platform 101 alone and/or in combination with processors 142 of remote servers 140 and processors 120 of mobile device 118. In some embodiments, processors 102, 120, 142 may include one or more of a digital processor, an analog processor, a digital circuit designed to process information, an analog circuit designed to process information, a state machine, and/or other mechanisms for electronically processing information. Although processors 102, 120, and 142 are shown in FIG. 1 as single entities, this is for illustrative purposes only. In some implementations, processors 102, 120, 142 may include a plurality of processing units. These processing units may be physically located within the same device (e.g., light therapy platform 101), or may represent processing functionality of a plurality of devices operating in coordination (e.g., mobile device 118 and/or remote servers 140).

Memories 104, 122, and/or 144 may include (not shown in FIG. 1) non-transitory machine-readable instructions configured for executing the exemplary embodiments described herein. Non-transitory machine readable instructions may include program instructions in source code, object code, firmware, executable code or other formats for performing the exemplary embodiments described herein. In some embodiments, memory 104 may include conventional computer system RAM (random access memory), ROM (read only memory), EPROM (erasable, programmable ROM), EEPROM (electrically erasable, programmable ROM), Flash memory, and/or magnetic or optical disks or tapes.

In some embodiments, I/O processing circuitry 106 may include one or more storage buffers, data registers, latches, CMOS inverters, interrupt/polling circuitry, timestamping circuitry, and/or other solid-state circuitry configured to receive and process raw data from sensors 108, 109 and communicate sensor data to processor 102. In one embodiment, I/O processing circuitry 106 may be configured to communicate audio alerts and/or visual indicators to a user via audible output 110 and visual indicators 111, respectively, which is described in further detail below.

In some embodiments, user interface 107 may include physical switches and/or buttons. User interface 107 may be configured to toggle power to the light control platform 101 via actuating a physical switch or button. For example, a subject may toggle user interface 107 to switch light therapy platform 101 on and off entirely. In some embodiments, a subject using light therapy platform 101 may control radiation generators 112 and/or light control valve 114, via user interface 107. For example, a subject may decide to override the light control plan and switch off components of light therapy platform 101 (e.g., radiation generators 112 and/or light control valve 114 among others). For example, a subject may decide to turn radiation generators 112 off by pressing a particular button of user interface 107 in order to override the light control plan. In some embodiments, as discussed in further detail below, user inputs are utilized to optimize the light control plan.

In some embodiments, light control system 100 may include physiological sensors 108, location sensors 109, and/or environmental sensors 113. Sensors 109, 108, 113 may be designed to assess parameters and information in the environment around the user, which is discussed in further detail below. In some embodiments, physiological sensors 108 may be coupled to and/or be part of light therapy platform 101, or physiological sensors 108 may be separate from, and in communication with light therapy platform 101, mobile device 118, and/or servers 140, for example. Light control system 100 may be configured to collect physiological data of the subject via physiological sensors 108. Physiological sensors 108 may be configured to generate output signals conveying physiological data of the subject. In some embodiments, physiological sensors 108 may include one or more of: a gyroscope, an accelerometer, a camera, a photoplethysmographic (PPG) sensor, a pupilometry sensor, an eye movement sensor, a heart rate variability (HRV) sensor, an ambient light sensor, a proximity sensor, a electroencephalogram (EEG) sensor, a electromyography (EMG), an electrooculography (EOG) sensor, an electrocardiogram (EKG) sensor, galvanic skin response (GSR) sensor, a heat-flow sensor, and/or a temperature sensor. Sensors 108, in some embodiments, may be mounted and integrated within the frame of light therapy platform 101, which is discussed in further detail below in the discussion of FIGS. 2A and 2B. In some embodiments, physiological data may include sleep data, fatigue levels, blink rate, alertness levels, body temperature of the subject, pupilometry, pulse and HRV, eye motion, and/or monitoring the direction and dynamics of angle of gaze, which is discussed in further detail below.

In some embodiments, gyroscope/accelerometer based physiological data of the subject may include head nod detection data acquired from accelerometers and/or gyroscopes. The gyroscope(s)/accelerometer(s) may be mounted within the frame of light therapy platform 101, which is discussed further in FIGS. 2A and 2B below. In some embodiments, the frequency of head nods of a subject may be utilized to determine the alertness/fatigue levels of the subject. In some embodiments, a gyroscope and/or an accelerometer may output motion data configured to track motion of the subject's head. Movements of the subject's head may include movement that corresponds to vertical translational movement that results from walking, running, and the like. Movements of the subject's head may correspond to horizontal rotational movement that corresponds to looking left, right, up, or down. In some embodiments, gyroscopes and/or accelerometers of physiological sensors 108 may be configure to transmit raw movement data of the subject to processor 102, via I/O processing circuitry 106. Processor 102 may be configured to filter (e.g., band pass filtering) the raw movement data and identify head nods of the subject which correspond to the subject falling asleep.

In some embodiments, one or more of the cameras, proximity sensors, and or pupilometry sensors may be utilized to determine blink data of the subject and gaze detection. Proximity sensors and/or cameras may detect movement of the eyelids for sensing blinking of the subject. In some embodiments, cameras and pupilometry sensors may detect the direction and length of time a subject looks at a particular direction. For example, detecting a lack of change in the direction of the pupils may indicate a gaze corresponding to lower alertness levels and increased fatigue. In some embodiments, blink/gaze data of the subject may be utilized for determining fatigue/alertness levels of the subject. In some embodiments, blink rate may include determining the rate of blinking, the blink intensity (i.e., elapsed time per blink), the time between blinking, and/or the lapsed time per blink. In some embodiments, tracking the rate of blinking, the blink intensity (i.e., elapsed time per blink), the time between blinking, and/or the lapsed time per blink may provide data for determining the change in the rate of blinking, blink intensity, and the time between blinking, and/or elapsed time per blink.

In some embodiments, a PPG sensor, a HRV sensor, and/or a temperature sensor, may be utilized to determine the sleep data of the subject. A HRV sensor may be utilized to determine heart rate variability of the subject. A PPG sensor may aid in the determination of heart rate variability and also provide blood pressure information of the subject. Blood pressure and HRV may be utilized to determine a sleep state of the subject. As is known in the art, by determine the variability of the subjects heart rate, a sleep state of the subject (i.e., awake or asleep) may be determined.

Physiological goals, physiological data, and time data alone may not be sufficient to optimally regulate blocking. For example, a subject spending time indoors during lunch time may need less blocking than a subject spending lunchtime outdoors. While a subject who is outdoors on a sunny day may need more blocking than a subject that is outdoors on an overcast day. Thus, in some embodiments, environmental sensors 113 may be configured for environmental sensing. Environmental sensors 113 may sense: temperature, humidity, illumination (e.g., illuminance and spectrum), landmarks and objects including the placement and motion of landmarks and objects, user head and body motion based on observed motion of the environment, environmental light source characterization (e.g., illuminance and spectrum), and external therapy light sources (e.g., lamp 156). For example, in some embodiments, environmental sensors 113 may measure and convey ambient data (intensity/spectrum of the environmental light/radiation), which may be used to automatically adjust light control valves 114 to block or reduce ambient radiation. In some embodiments, environmental sensors 113, physiological sensors 108, and/or locations sensors 109 may be configured to transmit raw data corresponding to physiological data of the subject to I/O processing circuitry 106.

In some embodiments I/O processing circuitry 106 may receive raw data from physiological sensors 108, location sensors 109, and/or environmental sensors 113 (described below), and associate the raw data with time data (e.g., a time stamp or other time data such as calendar dates, month/year, time zone data, and the like). In some embodiments, the light control plan for the subject based on the physiological goals of the subject, the physiological data, environmental data, and time data. In some embodiments, processors 102, 144 may generate output signals conveying the time data, the time data being associated with the output signals from physiological sensors 108, environmental sensors 113, and location sensors 109.

In some embodiments, I/O processing circuitry 106 may be configured to buffer the raw data and perform signal processing techniques to remove unwanted noise and artifact present in the signal output by sensor 108. In some embodiments, light control plan for the subject based on the physiological goals of the subject, the physiological data, environmental data, and time data. In some embodiments, processors 102, 144 may generate output signals conveying the time data, the time data being associated with the output signals from physiological sensors 108, environmental sensors 113, and location sensors 109.

As discussed in further detail below, in some embodiments physiological data of the subject may be utilized to determine fatigue levels, alertness levels, and/or an estimated circadian phase of the subject. For example, physiological sensors 108 may be configured to collect biofeedback including blink/gaze detection. In these embodiments, physiological sensors may include cameras and/or other components, for example. Blink/gaze detection data may be collected by utilizing cameras that may be configured to observe the eyes of the subject and detect blinking of the subject eyelids and gaze of the subject's eyes. The gaze of the subject eyes, in some embodiments, may correspond to a distance from the each lower eyelid to a respective upper eyelid. By measuring the number and frequency of blinking and also the distance each eyelid is apart in relation to the subject's nominal eyelid separation distance may be utilized to determine Fatigue/Alertness level, which is discussed in further detail below.

In some embodiments, location sensors 109 may be configured to generate output signals conveying location data corresponding to a geographic location of the subject. In some embodiments, location sensors 109 may include one or more of: an accelerometer, a magnetometer, and/or a GPS sensor. The geographic location of the subject may be utilized in conjunction with physiological data and physiological goals to determine a current circadian phase and implement a light control plan, which is discussed in further detail below. In some embodiments, I/O processing circuitry 106 may be configured to receive physiological data and locational data of the subject via sensors 108, 109, buffer and condition raw sensor data for removing noise and artifact, and communicate such data to processor 102.

In some embodiments, visual indicators 111 may include one or more multicolored LEDs and/or a liquid crystal display (LCD). Visual indicators 111, may be utilized to help inform the user of recommended light control and/or other advice to observe at a particular current time, or at future times, of the day. For example, visual indicators 111 may utilize a red LED alert to indicate to the subject that it is time to block blue light and may utilize a green LED alert to indicate that the subject that it is time to receive blue light. In some embodiments, visual indicators 111 may include a LCD screen and display a message to indicate to the user that it is time to block or receive blue light. Thus, in some embodiments, the user may be able to remove light therapy platform 101, for example, if outdoors under bright lighting condition, when a LED indicator of visual indicator 111 can illuminate, and/or an audio alert the audible output 110 may sound, to inform the user it is time to don light therapy platform 101, and/or other components (e.g., components 150, 154, 156), in order to increase, block, or reduce blue light, for example, utilizing light control valves 114 and/or radiation generators 112.

In some embodiments, radiation generators 112 may be configured to generate therapeutic light radiation onto the eyes of the subject. In some embodiments, therapeutic light radiation may include light having wavelengths between 450 nanometers through 545 nanometers (i.e., blue-to-blue/green light). In other embodiments, therapeutic light radiation may include light having wavelengths corresponding to 546 nanometers through 750 nanometers (i.e., green, amber, red light).

In some embodiments, radiation generators 112 may be configured to receive commands from processor 102. Radiation generators 112 may include hardware and software drivers configured to receive commands from processor 102 and actuate radiation generators 112 in accordance with the received commands. In some embodiments, radiation generator 112 may include one or more radiation generators that may be configured to emit generated radiation. Radiation generators 112 may generate therapeutic light radiation. In one embodiment, therapeutic light radiation may correspond to at least blue light radiation within the melanopsin band of light spectrum. In another embodiment, radiation generators 112 may be configured to emit wavelengths of light blended with blue light or blended without blue light, for example such as red light that has been shown to increase attentiveness even though it does not suppress melatonin or change circadian phase.

In yet another embodiment, radiation generators 112 be configured to emit wavelengths corresponding to 450 nanometers through 545 nanometers (i.e., blue-to-blue/green light). In other embodiments, radiation generators 112 may be configured to wavelengths corresponding to 546 nanometers through 750 nanometers (i.e., green, amber, red light).

Light control valve(s) 114 may be configured to block or reduce blue light ambient radiation reaching eyes of the subject. Light control valve 114 may be configured to receive commands from processor 102. Light control valve 114 may include hardware and software drivers configured to receive commands from processor 102 and actuate light control valve 114 in accordance with received commands. In some embodiments, light control valve 114 may include an optical lens or shield that blocks blue light and other shorter wavelengths. In some embodiments, blocking blue light may include blocking ambient light having wavelengths of between 450 nanometers and 495 nanometers. In some embodiments, blocking light of shorter wavelengths than blue light may include blocking ambient light having wavelengths less than 400 nanometers (i.e., including UV light). While the light being passed by the lens/shield includes ranges between: 401 nanometers and 449 nanometers, and/or between 546 nanometers and 750 nanometers.

In one embodiment, light control valve 114 may be implemented utilizing static optical filter material. In another embodiment, light control valve 114 may include dynamic phase-change filtering material that changes between blue-blocking and blue-passing phases under electric control. In some embodiments, light control valve 114 may include one or more solar lenses. Solar lenses may be configured to filter wavelengths corresponding to blue light radiation and produce power from the filtered wavelengths. Power produced from solar lenses may be utilized by system 100 as a power source, which is described in further detail below.

As shown in FIG. 1, mobile device 118 may include processor 120, memory 122, mobile transceiver 124, mobile UI 126, display 120, and/or other components. Mobile transceiver 124 may be configured to communicate with light therapy platform 101 directly via transceiver 116, or indirectly via network 120. Mobile device 118 may include a smart phone, tablet, smart watch, laptop computer, notebook, desktop computer or any other computing device capable of establishing a connection with the Internet and/or other communication networks.

In some embodiments, user interface 126 may include a graphical user interface 126 including display 128 that may be provided on mobile device 118 such as that illustrated in FIG. 1, In one of the embodiments, user interface 126 may be provided on a desktop device (not shown) or other device that can present a graphical user interface. In another embodiment, user interface 126 may be provided on a remote device (not shown) that can accept user input, for example through gestures, motion, or other mechanism that can be used to detect and or register desired input of a user. Mobile UI 126 may include one or more buttons and/or switches configured toggle display 128 on and off. UI 126 and display 128 may be configured to communicate messages and receive input from a subject. In one exemplary embodiment, display 128 may include an LCD touchscreen display configured to display a keyboard to a user of mobile device 118 and receive user inputs, for example, physiological goals of the subject. In another exemplary embodiment, display 128 may include an organic light emitting diode (OLED) display type or other displays types (e.g. LED, etc.). Mobile device 118 may be configured to receive physiological goals of the subject via mobile UI 126.

In some embodiments, the physiological goals of the subject may include goals related to adapting to shift-work, reducing the effect of jet lag, maximizing drug efficacy, re-aligning a circadian phase to meet a desired sleep/wake schedule, achieving increased attention and performance, mitigating seasonal affective disorder, improving winter blues, improving mood, providing sleep consolidation, and/or reducing the symptoms of psychological disease or syndromes. In some embodiments, physiological goals of the subject may include the length of time the subject has to complete a circadian phase shift. For example, the subject may need to be completely adjusted in a relatively short amount of time or may have ample time to complete a circadian shift.

Having received physiological goals of the subject, mobile device 118 may be configured to communicate such goals to remote server 140 and/or light therapy platform 101 via network 120 and/or directly via transceiver 116. As shown in FIG. 1, in some embodiments, light therapy platform 101, may be configured to communicate directly with mobile device 118, via transceiver 116. In one embodiment direct communication between light therapy platform 101 and mobile device 118 may be facilitated utilizing RF near wave communication techniques, for example utilizing Bluetooth™ or BLE™.

Figure 2A:
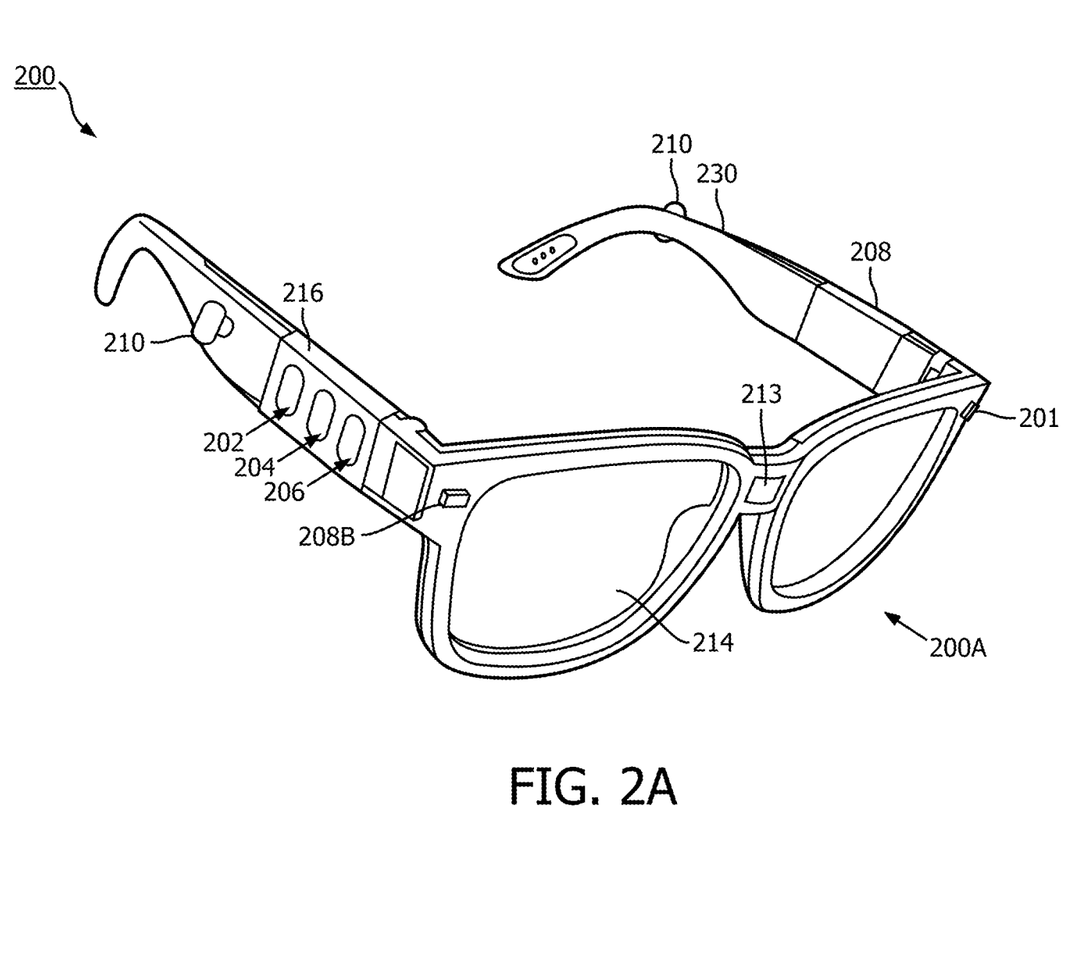
FIGS. 2A and 2B are front and rear perspective views, respectively, of an exemplary illustration of light control platform controlling light exposure for use in light control system in accordance with one or more embodiments.
Figure 2B:
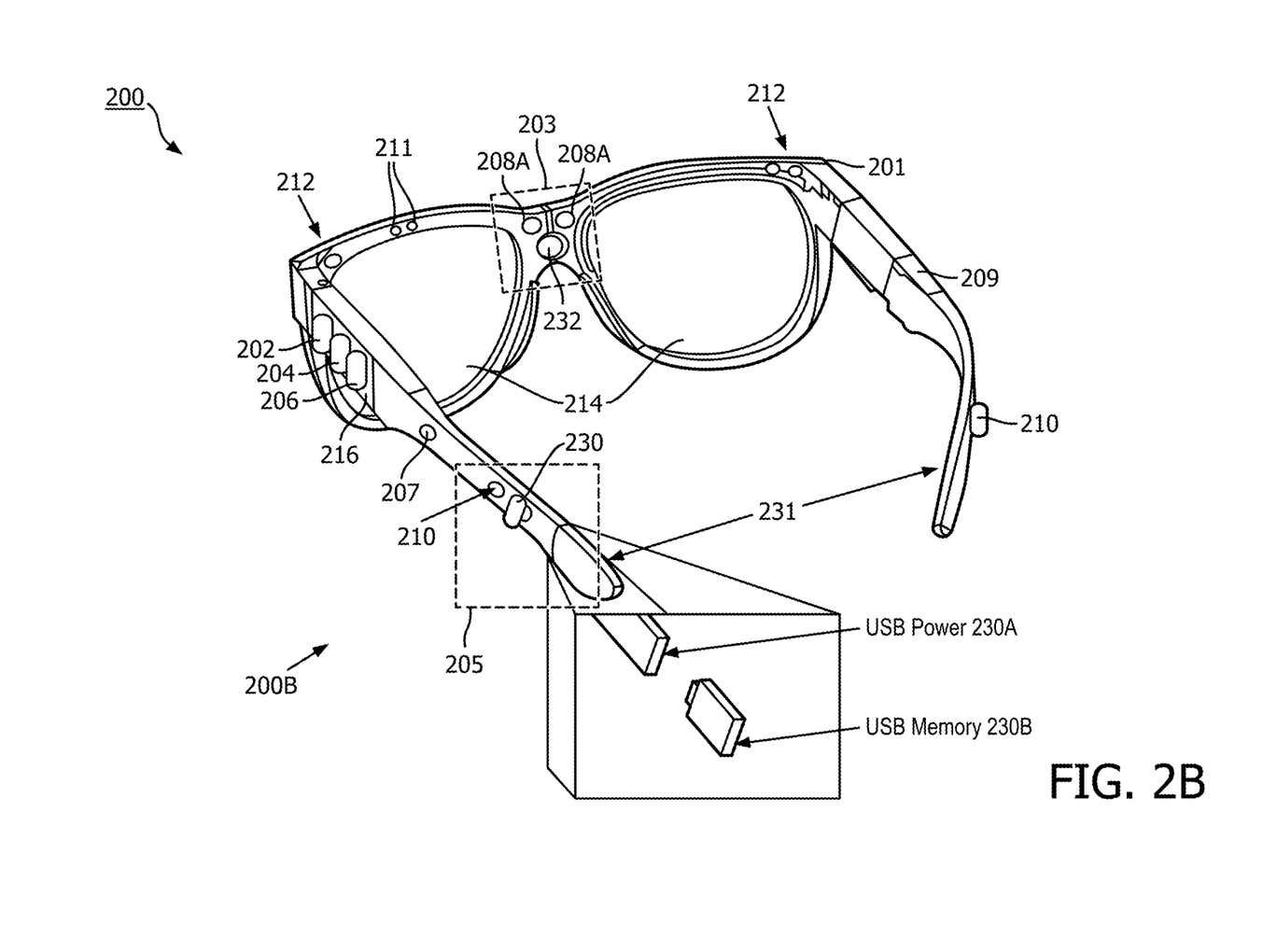

Referring now to FIGS. 2A and 2B, these figures depict an exemplary light therapy platform 200 showing front a view 200A and a rear view 200B. Light therapy platform 200 may correspond to light therapy platform 101 of FIG. 1, of which similarly labeled parts and numbers correspond to similar features having similar functionality. As shown ins FIGS. 2A and 2B, light therapy platform 200 may be configured to provide light therapy to a subject by providing a comfortable delivery mechanism for light therapy, and may deliver the light therapy to the subject while the subject is awake and active and also asleep, in the process of going to sleep, and/or waking from sleep.

As shown in FIGS. 2A and 2B, in some embodiments, light therapy platform 200 may correspond to a pair of glasses configured to be worn on the subject's head. Light therapy platform 200 may include glasses frame housing 201. In some embodiments, glasses frame housing 201 may correspond to a sunglass frame, which is configured for housing components of light therapy platform 200. In one embodiment, glasses frame housing 201 may be configured for housing processor 202, memory 204, I/O processing circuitry 206, platform UI 207, physiological sensors 208, location sensors 209, environmental sensors 213, audible output 210, visual indicators 211, radiation generators 212, light control valves 214, transceiver 216, and power module 230.

In some embodiments, processor 202 may correspond to processor 102 of FIG. 1. Processor 202 may be configured to provide information processing and/or system control capabilities in light therapy platform 200 alone and/or in combination with processors 142 of remote servers 140 and processors 120 of mobile device 118, of FIG. 1. In some embodiments, location sensors 209 may be configured to generate output signals conveying location data corresponding to a geographic location of the subject. In some embodiments, location sensors 209 may include one or more of: an accelerometer, a magnetometer, and/or a GPS sensor mounted internally within glasses frame housing 201. The geographic location of the subject may be utilized in conjunction with physiological data and physiological goals to determine a current circadian phase and implement a light control plan, which is discussed in further detail below.

In some embodiments, I/O processing circuitry 206 may be configured to receive physiological data and locational data of the subject via sensors 208, 209. I/O processing circuitry 206 may correspond to I/O processing circuitry 106 of FIG. 1. In some embodiments, I/O processing circuitry 206 may be configured to buffer and condition raw sensor data. Conditioning raw sensor data may include for removing noise and artifact. I/O processing circuitry 206 may be configured to communicate raw sensor data to processor 202 for determining a light control plan.

In some embodiments, physiological sensors 208 may correspond to physiological sensors 108 of FIG. 1. Physiological sensors 208 may include sensors for biofeedback. In one embodiment, physiological sensors 208 may be configured for monitoring bio-signals such as sleep data, fatigue levels indicated by blink rate, body temperature, and/or alertness levels. In one embodiment, physiological sensors 208 may include a temperature sensor integrated within or mounted on temple tip 205, for example. The temperature sensor of physiological sensors 208 may be configured to measure the body temperature of the subject.

In some embodiments, physiological sensors 208 may include a near range proximity sensor on/near a (e.g., the top) side of the glasses facing toward the eyes of the subject and configured for detecting eye blinking. In some embodiments, blink and gaze detection may be implemented via one or more of pupilometry, pulse and HRV, eye motion, and monitoring the direction and dynamics of angle of gaze. Based on the rate of blinking a subject falling asleep may be detected and woken in accordance with an optimal light control therapy plan.

In one embodiment, light therapy platform 200 may be configured for monitoring characteristics of light reaching the eyes of the subject, and/or ambient light beyond light control valve 214. Physiological sensors 208 may include a light sensor or camera 208A mounted on glasses frame 201, for example on/near bridge 203 facing toward the subject's eye, as shown in FIG. 2B. In some embodiments, light sensor or camera 208A of physiological sensors 208 may be configured to assess relative intensities of (e.g., key) wavelengths over the visible and non-visible spectrum. Physiological sensors 208 may include a camera used for collecting other information such as pupil size and dynamics, eye motion and blink detection, as discussed above.

In one embodiment, physiological sensors 208 may include sensor camera 208B that may be disposed to view light characteristics in the field (e.g., ambient environment) in front of, or around, the subject, as shown in FIG. 2A. For example, referring to FIG. 2A, physiological sensors 208 may include a light sensor and/or camera 208B facing away from the subject's eye, on the exterior facing portion of sunglass frame 201, toward the ambient environment. The subject may be given an indication or reading that can inform the subject about ambient lighting conditions and/or light spectrum and intensity reaching the eyes, for example via mobile UI 126 of mobile device 118, or indicated to the user by a visible indicator 111, 211 on the therapy platform 101, 200.

In some embodiments, physiological sensors 208 may include a gyroscope and/or an accelerometer that is integrated into glasses frame housing 201 such that nodding may be detected when a subject is dozing and a haptic feedback (not shown) could be provided to wake the subject up if the light control plan requires staying awake. Referring to FIG. 2B, in some embodiments, gyroscope/accelerometer of physiological sensors 208 may be internally mounted within bridge 203. For example, gyroscopes and/or accelerometers of physiological sensors 208 may be configured to detect head nods of the user when wearing light therapy platform 200. By detecting head nod severity/intensity, a subject's fatigue level and/or alertness levels may be deduced. In some embodiments, the severity and intensity of the head nod may correspond to a measured acceleration of platform 200 in conjunction with a degree of angular rotation experienced by the gyroscope of platform 200. The frequency of the head nod may be derived from the accelerations. The frequency of head nods considered to be fatigue may be measured by the amount of head nods per minute that exceed a predetermined frequency at awakening state. The range of the motion of a head nod may be measured via the angular velocity detected by the gyroscope. The range of the motion combined with the frequency of head nods may be used for determining the severity and the intensity of the head nod. In one embodiment, the motion of the eye (e.g., saccadic motions) may be measured, which may indicate mental physiological changes of the user due to tiredness or fatigue.

In some embodiments, light therapy platform 200 may include locations sensors 209. Location sensors 209 may correspond to location sensors 109 of FIG. 1. Location sensors 209 may be configured to monitor and track the geographic location of a subject. Location sensors 209 may include a Global Positioning System (GPS) and gyroscopes and/or accelerometers configured to sense a geographic location and movement of the subject. As described in further detail below, the geographic location and movement of the subject may be utilized by the light control plan in order to determine a circadian phase of the subject.

In some embodiments, light therapy platform 200 may include environmental sensors 213. Environmental sensors 213 may correspond to environmental sensors 113 of FIG. 1. Environmental sensors 213 may sense: temperature, humidity, illumination (e.g., illuminance and spectrum), landmarks and objects including the placement and motion of landmarks and objects, user head and body motion based on observed motion of the environment, environmental light source characterization (e.g., illuminance and spectrum), and external therapy light sources (e.g., lamp 156).

As shown in FIGS. 2A and 2B, light therapy platform 200 may include radiation generators 212 which are mounted to glasses frame 201 on a side that faces the subject during use. Radiation generators 212 may correspond to radiation generators 112 of FIG. 1. Radiation generators 212 may be configured to emit therapeutic radiation onto the eyes of the subject at wavelengths that are configured to provide a therapeutic effect on the subject when the emitted in accordance to a light control plan. In some embodiments, radiation generators 212 may include a two-lead semiconductor light source, for example, one or more of light emitting diodes (LEDs). In some embodiments, LEDs may include RGB LEDs consisting of one red, one green, and one blue LED and may be configured to independently adjust all three in order to produce light radiation of varying wavelengths, for example between 760-400 nanometers. In some embodiments, radiation generators 212 may include phosphor-based LEDs, organic light-emitting diodes (OLEDs), and/or quantum-dot LEDs having phosphors of different colors to produce light radiation of varying wavelengths, for example, between 760-400 nanometers.

In accordance with a light control plan, radiation generators 212 provide specific characteristics and timing of light that the subject experiences during the course of a day. Radiation generators 212 may correspond to radiation generators 112 of FIG. 1. Wavelengths emitted by radiation generators 212 correspond to therapeutic light including wavelengths that activate the non-visual tract of the optic nerve, which are associated with controlling the body's circadian clock and/or provide a therapeutic effect such as improving mood. In some embodiments, radiation generators 212 may emit radiation in various wavelengths in order to supplement ambient environment light radiation at key times of the day.

Radiation emitted by radiation generators 212 (e.g., as controlled by processor 102 shown in FIG. 1) may be directed towards the eyes of the subject in radiation fields having relatively uniform luminance as perceived by the subject. For example, in one embodiment, the luminance of the radiation emitted radiation generators 212, the size of the uniform field of radiation formed by radiation generators 212 may correspond to the size of the eye of the subject. In one embodiment, radiation generators 212 may emit continuous therapeutic radiation, intermittent radiations, and/or a combination of continuous and intermittent therapeutic radiation in accordance with a light control plan. In some embodiments, prior to adjusting radiation generators 212 or light control valve 214, a warning or functional transition of the light control valve and/or radiation generators 212 may be implemented so that a subject is not startled or may override or pause the transition to the new function. For example, giving an audio alert, via audible output 210, before the therapeutic illumination is started or gradual ramping of light to allow acclamation or a chance to delay the illumination function.

Receipt of radiation at particular wavelengths has an impact on the circadian rhythms of subjects. As such, light therapy platform 200 is configured to provide radiation to the subject at these wavelengths at predetermined intensities and/or times in accordance with a light control plan. The reception of such radiation (e.g., in ambient light) at times that are out of synch with the administration of radiation according to the light control plan may have a deleterious impact on the therapeutic benefits received by the subject from use of light therapy platform 200.

In order to reduce the potentially deleterious impact of ambient light that becomes incident on the eyes of the subject, in one embodiment, light therapy platform 200 includes light control valves 214 (e.g., controlled by processor 102, 202 shown in FIG. 1). Light control valve 214 may correspond to light control valve 114 of FIG. 1. Light control valves 214 may be configured to block counter-productive light from entering the eyes of the subject at various (e.g., "the wrong") times of the day and allow that same light to enter at other (e.g., "the right") times of the day. In one embodiment, light control valves 214 may be configured to block ambient radiation that, if allowed to reach the eyes of the subject, would interfere with the light control plan provided to the subject by light therapy platform 200. Light control valves 214 are further configured to enable ambient radiation to pass through valves 214, which does not interfere with the light control plan provided to subject by light therapy platform 200.

For example, in one embodiment, light control valves 214 comprise an optical shield configured as passive filters that block ambient radiation having a wavelength in a predetermined wavelength range. The predetermined wavelength range is the range of wavelengths at which ambient light would interfere with the light control plan provided by light therapy platform 200. By way of non-limiting example, in one embodiment, the predetermined wavelength range includes wavelengths shorter than or equal to 580 nm. In one embodiment, the predetermined wavelength range includes wavelengths between about 580 nm and about 410 nm. Blocking light in the predetermined wavelength, while reducing the deleterious impact of ambient light on the subject, will still allow the subject to see through light control valves 214. For example, the portion of the visible spectrum outside of the predetermined wavelength (e.g., >580 nm) will pass through light control valves 214, thereby enabling the subject to see and continue normal activity. In some embodiments, optical light control valve(s) 214 may include an optical lens configured as a dynamic optical lens, which may be configured to filter various wavelengths of ambient light under electric control. The electric optical lenses may be configured to automatically adjust filtering various wavelengths of ambient radiation in order to meet goals for circadian management and/or photo-biological effect.

In some embodiments power module 230 may include a mounted solar cell on outer frame 201 that may be configured to provide charging for a rechargeable battery (not shown in FIGS. 2A and 2B) included in power module 230. In some embodiments, bridge 203 of glasses frame housing 201 may be sufficiently wide (for example) in order to house or otherwise couple with a (e.g., flat) NiMH or Lithium Ion rechargeable battery 232, for example. As shown in FIGS. 2A and 2B, in one embodiment, power module 230 may be positioned on the temple tip portion 231 of frame 201 as a USB power connection 230A, which, in some embodiments may include a USB flash memory device 230A housed in the end of temple tip 231. USB port 230A may be configured to be connected to a USB charger directly or via a USB cable. In some embodiments, frame 201, temple tips 231, and/or bridge 203 and nose pads (not shown) may be configured for functioning as Qi certified wireless charging receivers. In one embodiment, optical light control valves 214 may include photovoltaic thin film cells, which may be tuned to filter blue wavelengths to produce power. In yet another embodiment, power module 230 may be configured to charge a battery via motion, inductive charge coupling, and/or wireless charging via an RF carrier.

Figure 3:
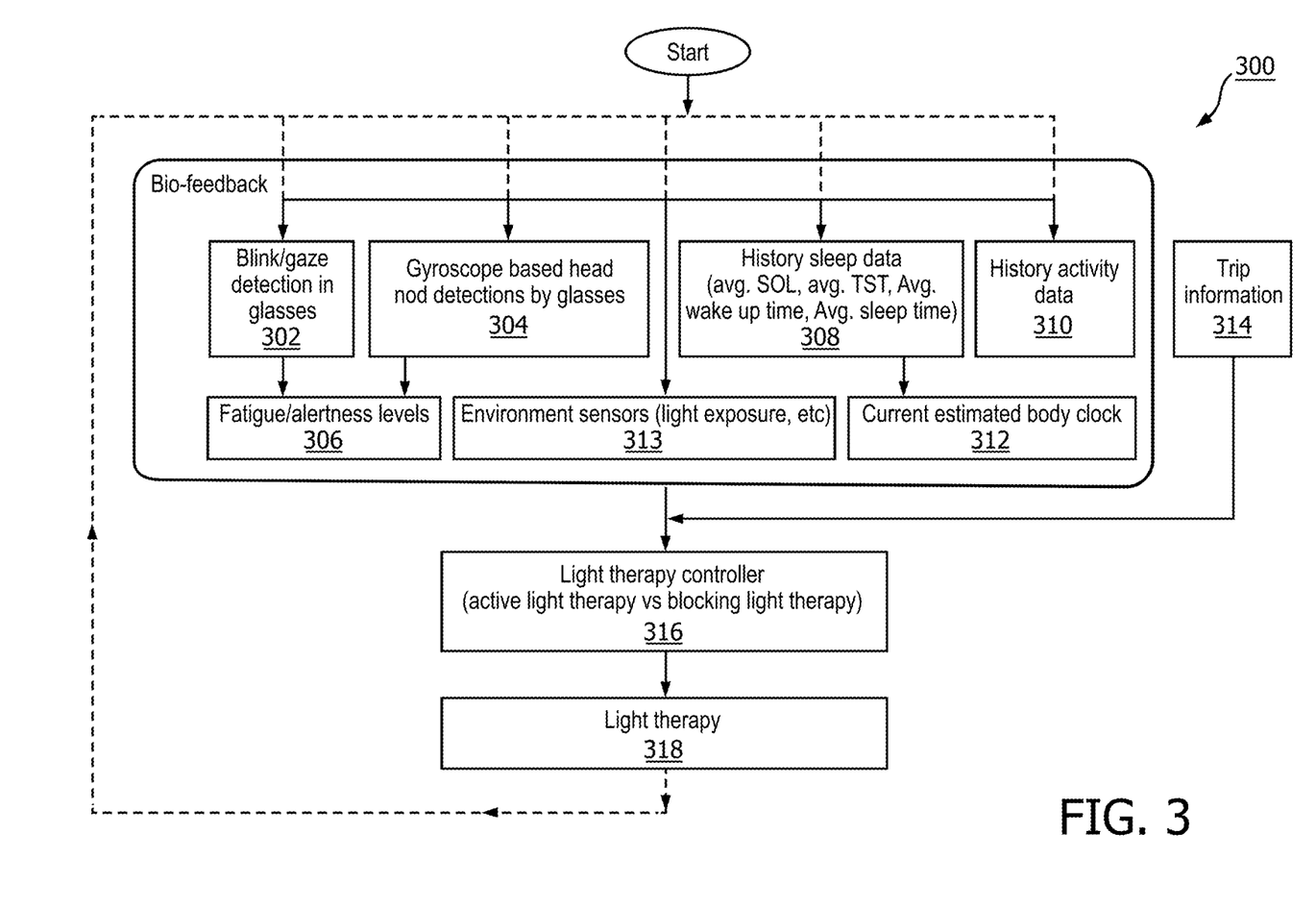
FIG. 3 illustrates a flowchart describing a method for controlling light exposure in accordance with one or more embodiments.

Referring now to FIG. 3 in conjunction with FIG. 1 and FIGS. 2A and 2B, FIG. 3 depicts a method 300 for determining an optimal light control therapy plan based on physiological data, time data, environmental data, and location data. For example, the operations of FIG. 3 describe on demand light control settings based on a specific travel schedule of the subject utilizing light therapy platform 101 (FIG. 1), 200 (FIGS. 2A and 2B), as discussed above. FIG. 3 illustrates determining day-long or multiple-day light control to meet circadian phase or other physiological coals. In some embodiments, a light control plan (as in this example) may implement various light controls having a date, time, duration, and light characteristics (spectrum and strength), based on the travel schedule of the subject. Accordingly, in some embodiments, location sensors 109 (FIG. 1), 209 (FIGS. 2A and 2B) may be configured to generate output signals conveying location data corresponding to a geographic location of the subject. Determining a light control plan may include determining the light control plan for the subject based on the physiological goals of the subject, physiological data, environmental data, time data, and location data. In some embodiments, light therapy system 100 may be configured to measure/estimate the actual light exposure to the user (including spectrum) that the user experiences while awake. Specialized light exposure during sleep or napping may be sensed and/or accounted for. Taking all information into account, the total light exposure history may be saved and/or used to calculate the accumulated phase and amplitude changes to the circadian system over a particular time period.

As discussed above physiological sensors 108 (FIG. 1), 208 (FIGS. 2A and 2B) and location sensors 109 (FIG. 1), 209 (FIGS. 2A and 2B) may be configured to collect location data and physiological data of the subject. In one embodiment, I/O processing circuitry 106 (FIG. 1), 206 (FIGS. 2A and 2B) may be configured to associate time data with physiological data, environmental data, and location data collected by physiological sensors 108, 208, environmental sensors 113, 213, and location sensors 109, 209, respectively. For example, in one embodiment, I/O processing circuitry 106 may be configured to receive raw data from sensors 108, 208, 109, 209, 113, 213 and time stamp the received data with the current time including the geographic time zone. In one embodiment, the geographic time zone may be deduced from information received by location sensors 109, 209.

As shown in FIG. 3, at an operation 302, processors 102 (FIG. 1), 202 (FIGS. 2A and 2B) may be configured for blink/gaze detection utilizing physiological sensors 108, 208 as described above. At an operation 304, processors 102, 202 may be configured to collect physiological data from physiological sensors 108, 208 to perform gyroscope-based head nod detection, utilizing physiological sensors 108, 208 as described above. At an operation 306, having received blank/gaze detection data (operation 302) and gyroscope based head nod detection data (operation 304), processors 102, 202 may be configured to determine fatigue/alertness levels based on blank and/or gaze detection data and gyroscope-based head nod detection data. In one embodiment, in addition to fatigue alertness levels 306, light control plan 300 may be configured to determine a current estimated body clock.

At an operation 308, processors 102, 202 may be configured to collect historic sleep data of the subject. Historic sleep data of the subject may be procured from previous use of light control system 100 (FIG. 1), for example system 100 may implement an initial calibration and training period in which a subject's sleep and activity data are monitored for a sufficient length of time to develop a baseline sleep and activity, which are then stored as sleep history data 308 and/or activity history data 310. In some embodiments, sleep history data 308 and historic activity data 310 may be procured from a third party via servers 140, or may be input by the subject via mobile UI 126 (FIG. 1).

In some embodiments, historic sleep data may include average sleep onset latency (e.g., time required for sleep onset), total sleep time, average wake-up time, average sleep time, number of sleep interruptions, sleep efficiency (e.g., total time spent sleeping per hour spent in bed), mean sleep latency (e.g., averaged time for sleep onsets), sleep cycle length, sleep state latencies (deepness of sleep states, i.e., REM and non-REM sleep), percentage of a sleep state during sleep (i.e., percentage of REM sleep vs non REM sleep), percentage of a sleep state during a sleep cycle, intra sleep wakefulness (e.g., the total time spent moving and awake divided by the total time spent in bed), total movement time, total sleep time, or total time in bed, or light exposure in the evening or during the sleep period (e.g., when rising to visit the bathroom). In some embodiments, historic sleep data may include subjective sleep quality data input by a user via a user interface (e.g., UI 126). Subjective sleep quality data may include response to interrogatories presented to the user via a user interface (e.g. UI 126)

At an operation 310, processors 102, 202 may collect historic activity data in order to determine a current estimated body clock. Historic activity data 310 may include activity data corresponding to geographic movement of the subject. In some embodiments, historic geographic movement of the subject may include time zones that the subject travels through. Historic activity data may include an average length of time a subject stays in the particular time zone, the frequency of traveling to particular time zones and/or geographic locations. For example, location sensor 109, 209 may be configured to provide geolocation tags and associate geolocation tags with a timestamp via I/O processing circuitry 106, 206. Geolocation tags and corresponding timestamps may be utilized by processors 102, 202 to determine historic activity data, and also for determining real-time adjustments to the light control plan, which is discussed in further detail below.

At an operation 312, processors 102, 202 may be configured to determine a current estimated body clock. A current estimated body clock may correspond to a particular circadian phase of the subject. At an operation 313, processors 102, 202 may be configured to input environmental information (e.g., environmental data including light exposure, via environmental sensors 113, 213) of the subject for determining active light therapy versus blocking therapy of a light control plan. At an operation 314, processors 102, 202 may be configured to input trip information of the subject for determining active light therapy versus blocking therapy of a light control plan. Trip information may include an anticipated travel itinerary including the local time of day at the destination, current time of day at a current location, anticipated duration of travel time to the destination. At an operation 316 processors 102, 202 may be configured to determine a light control plan that includes active light therapy and blocking light therapy based on fatigue/alertness levels, current estimated body clock, and trip information. An operation 318, processors 102, 202 may be configured to implement light therapy in accordance with a light control plan, for example by causing light control valves 114 (FIG. 1), 214 (FIGS. 2A and 2B) to block or reduce blue light ambient radiation based on the light control plan and/or generating, using the one or more radiation generators, therapeutic light radiation based on the light control plan. In some embodiments, light exposure history can be further utilized for dynamically adjusting the light control plan.

As shown in FIG. 3, after providing light therapy 318, in some embodiments, processors 102, 202 may be configured to utilize biofeedback to enable personalized and/or circumstantial functional improvement. This may be done by tracking how user inputs change over time based on therapy and providing feedback to the controller for timing light therapy based on changes to biofeedback of the user. For example, upon detecting improvements of sleep data such as higher total sleep time and lower sleep onset latency times, processors 102, 202 may provide dynamic adjustments to act of light therapy and blocking light therapy. A subject may also override the light control plan by manually controlling light blocking or light emitting functionality. Such user inputs may be incorporated by the light control plan to dynamically optimize and personalize light control plan based on a subject's historic usage. For example, in some embodiments, user inputs may include the user's subjective feedback on the sleep quality, which may be utilized for providing personalized functional improvements to the light control plan. Functional improvements may include, for example, increasing or reducing the intensity and duration of light therapy based on subjective sleep quality feedback of the user.

In some embodiments, user inputs for optimizing and personalizing light control plan may include short term and/or long term changes in work schedule (e.g., shift work) that may conflict with the originally designed light therapy plan and require adjustment of light control plan to continue or discontinue therapeutic light therapy for optimal physiological and mental performance. User inputs for optimizing and personalizing light control plan may include a change of desired and/or required peak performance time during a travel schedule that may induce jetlag symptoms and/or change travel duration in certain time zones, which may necessitate adjustment of the light therapy plan.

In some embodiments, processors 102, 202 may receive updated physiological data and updated location data and determine one or more adjustments of the light control plan based on the updated physiological data and the updated location data. Having received updated physiological data and updated location data, processors 102, 202 may be configured to adjust the blocking or reducing of the blue light ambient radiation and/or the generating of the therapeutic radiation based on the one or more adjustments of the light control plan. For example, a subject may decide to extend or delay a particular trip in a time zone, or may be delayed in transit on the way to a destination. Thus, light therapy system 100 may be configured to continuously transmit physiological data, environmental data, and location data in real time and continuously update the light control plan based on new or changing data. In some embodiments, a user may update the physiological goals and desire new physiological goals. These inputs are received by processors 102, 202 and implemented in an updated light control plan. By continuously updating data and improving the light control plan light therapy system 100 may achieve increased accuracy and efficiency in achieving the physiological subject.

Figure 4:
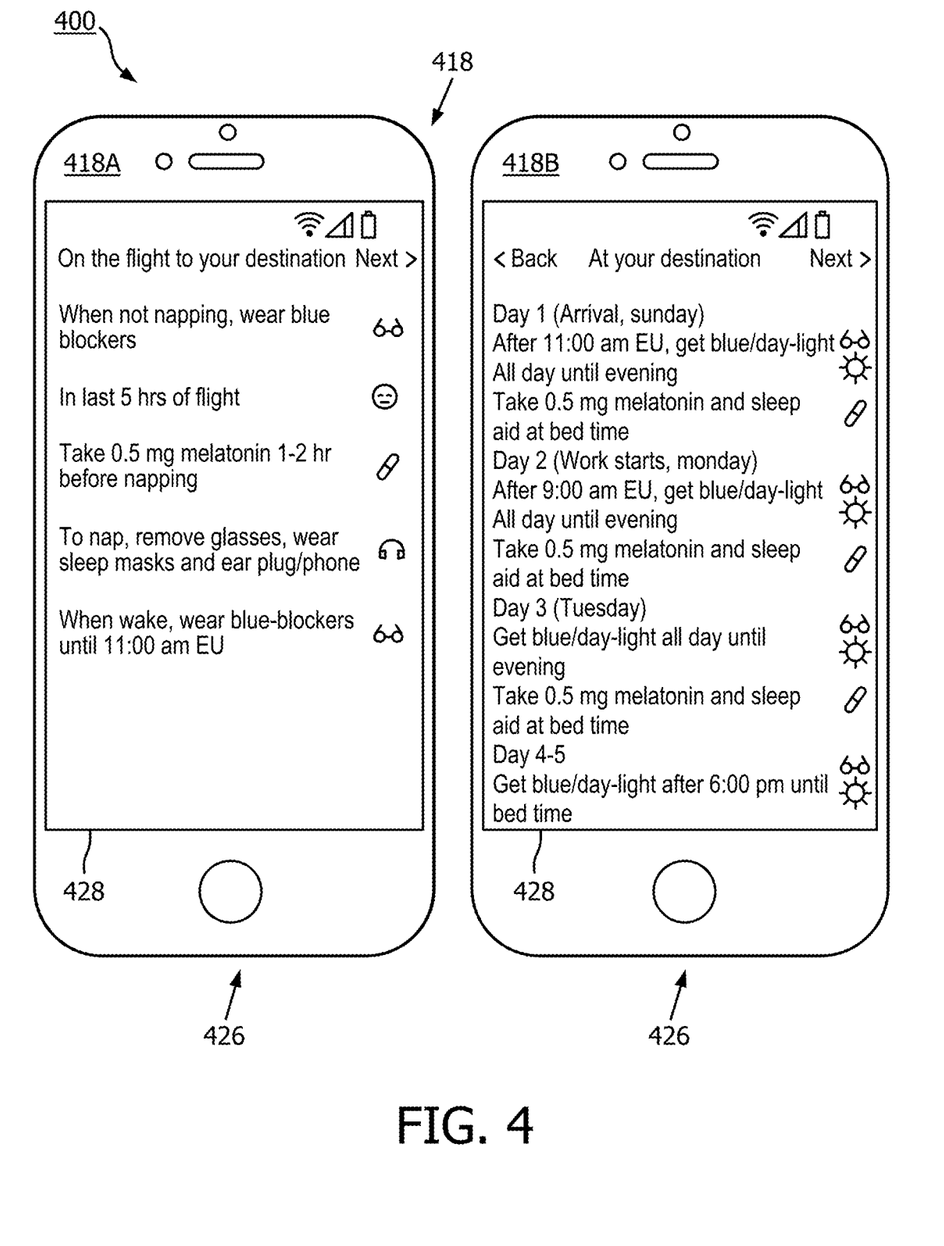
FIG. 4 illustrates an exemplary user interface of a system for controlling light exposure in accordance with one or more embodiments.

Referring now to FIG. 4 in conjunction with FIG. 1, FIGS. 2A and 2B, and FIG. 3. FIG. 4 depicts an exemplary mobile device 418, which may correspond to mobile device 118 of FIG. 1, in accordance with one or more embodiments. In some embodiments, mobile device 418 may be implemented as part of on demand light control settings based on a specific travel schedule of the subject utilizing light therapy platform 101 (FIG. 1), 200 (FIGS. 2A and 2B), as discussed above. In some embodiments, mobile device 418 may be configured to display day-long or multiple-day light control to meet circadian phase or other physiological goals of the subject, as discussed above in FIG. 3.

In some embodiments, user interface 426 may correspond to user interface 126 of FIG. 1. As shown in FIG. 4, user interface 426 may include display 428 configured to display a predetermined schedule corresponding to a light control plan, wherein the subject may be instructed to don light therapy platform 101 (FIG. 1), 200 (FIGS. 2A and 2B) and seek light (i.e., control valve light control valves 114, 214 may be configured to provide light and or control the filter characteristics of the lens or shield to permit light to pass). In some embodiments, processors 102, 120, 142 may determine adjustments to a light control plan and communicate and cause to display the adjustments of the light control plan utilizing display 128, 428. In some embodiments, processors 120 may be configured to display via display 128, 428 steps of therapy plan to a user and communicate adjustments to the light control plan based on user inputs, as discussed above in FIG. 3.

Figure 5:
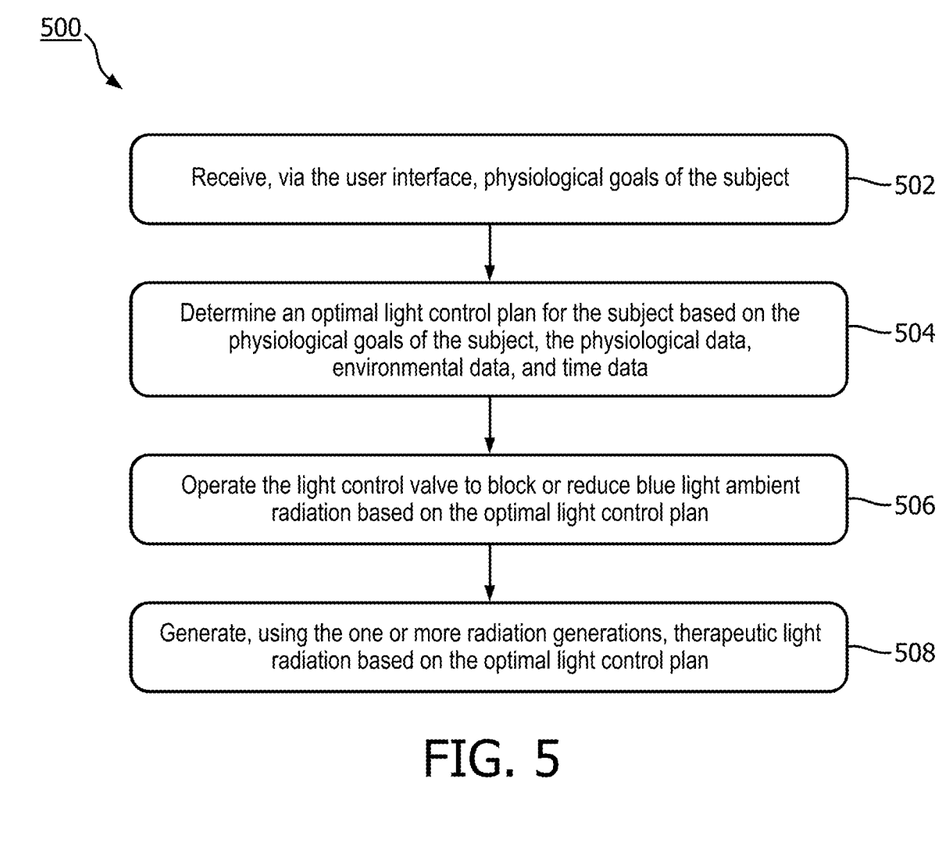
FIG. 5 illustrates a method for controlling light exposure in accordance with one or more embodiments.

Referring now to FIG. 5, FIG. 5 illustrates a method 500 for controlling light exposure for circadian phase management and/or light deficient disorders of a subject. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

At an operation 502, receive, via the user interface, physiological goals of the subject. In some embodiments, operation 502 is performed by a user interface the same or similar as user interface 126 of FIG. 1.

At an operation 504, determine a light control plan for the subject based on the physiological goals of the subject, the physiological data, environmental data, and time data. In some embodiments, operation 504 is performed by a processor the same or similar as processor 102 of FIG. 1.

At an operation 506, operate the light control valve to block or reduce blue light ambient radiation based on the light control plan. In some embodiments, operation 506 is performed by a light control valve the same or similar as light control valve 114 of FIG. 1

At an operation 508, generate, using the one or more radiation generators, therapeutic light radiation based on the light control plan. In some embodiments, operation 508 is performed by a radiation generator the same or similar as radiation generators 112 of FIG. 1

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to control light exposure for circadian phase management and/or light deficient disorders of a subject, the system comprising:
    a user interface;
    one or more physiological sensors configured to generate output signals conveying physiological data of the subject;
    a light control valve configured to reduce blue light ambient radiation reaching eyes of the subject;
    one or more radiation generators configured to generate therapeutic light radiation onto the eyes of the subject; and
    one or more processors in communication with the user interface, the one or more physiological sensors, the light control valve, and the one or more radiation generators;
    the light control valve comprising at least one of:
        a number of optical lenses controlled by the one or more processors to reduce the blue light ambient radiation based at least in part upon a light control plan from the one or more processors, and
        at least one of a hardware driver and a software driver configured to receive a command based at least in part upon the light control plan from the one or more processors and actuate the light control valve in accordance with the command;
    the one or more processors causing the system to:
        receive, via the user interface, physiological goals of the subject;
        determine the light control plan for the subject based on the physiological goals of the subject, the physiological data, environmental data, and time data;
        operate the light control valve to reduce the blue light ambient radiation based on the light control plan; and
        generate, using the one or more radiation generators, the therapeutic light radiation based on the light control plan.

2. The system of claim 1, further comprising one or more location sensors configured to generate output signals conveying location data corresponding to a geographic location of the subject, wherein the step of determining the light control plan comprises determining the light control plan for the subject based on the physiological goals of the subject, the physiological data, the environmental data, the time data, and the location data.

3. The system of claim 2, wherein the one or more processors further cause the system to generate output signals conveying the time data, the time data being associated with the output signals from the one or more physiological sensors, one or more environmental sensors, and the one or more location sensors.

4. The system of claim 2, wherein the one or more processors further cause the system to:
    receive updated physiological data and updated location data;
    determine one or more adjustments of the light control plan based on the updated physiological data and the updated location data; and
    adjust the reducing of the blue light ambient radiation and/or the generating of the therapeutic radiation based on the one or more adjustments of the light control plan.

5. The system of claim 1, wherein the one or more physiological sensors comprise one or more of: a gyroscope, a first accelerometer, a camera, a PPG sensor, a pupilometry sensor, a HRV sensor, an ambient light sensor, a proximity sensor, and/or a temperature sensor, and wherein the one or more location sensors comprise one or more of: a second accelerometer, a magnetometer, and/or a Global Positioning System (GPS) sensor.

6. The system of claim 1, wherein the light control valve comprises an optical shield, and wherein the therapeutic light radiation comprises at least blue light radiation, and wherein the one or more radiation generators is/are configured to emit generated radiation corresponding to at least blue light radiation in the melanopsin band of a light spectrum.

7. The system of claim 1, wherein the therapeutic light radiation comprises wavelengths shorter than blue light radiation.

8. The system of claim 1, wherein the physiological goals of the subject comprise adapting to shift-work, reducing an effect of jet lag, maximizing drug efficacy, re-aligning a circadian phase to meet a desired sleep/wake schedule, and/or reducing the symptoms of psychological disease or syndromes, and wherein the physiological data of the subject comprise fatigue levels, alertness levels, peak physiological and mental performance times, and/or an estimated circadian phase of the subject.

9. The system of claim 1, wherein the light control plan comprises one or more instructions corresponding to specific characteristics and timing of light radiation the subject experiences during the course of one or more days, the specific characteristics and timing comprising one or more of intensity level, wavelength, and/or duration.

10. The system of claim 1, further comprising one or more automated window blinds configured to reduce ambient light, one or more light therapy devices configured to generate the therapeutic light radiation onto the eyes of the subject, and/or one or more environment color control lamps configured to implement light therapy based on the light control plan.

11. A method for controlling light exposure for circadian phase management and/or light deficient disorders of a subject utilizing a light therapy system, the light therapy system comprising a user interface, one or more physiological sensors configured to generate output signals conveying physiological data of the subject, a light control valve configured to reduce blue light ambient radiation reaching eyes of the subject, one or more radiation generators configured to generate therapeutic light radiation onto the eyes of the subject, one or more processors in communication with the user interface, the one or more physiological sensors, the light control valve, and the one or more radiation generators, the light control valve having at least one of: a number of optical lenses controlled by the one or more processors to reduce the blue light ambient radiation based at least in part upon a light control plan from the one or more processors, and at least one of a hardware driver and a software driver configured to receive a command based at least in part upon the light control plan from the one or more processors and actuate the light control valve in accordance with the command, the method comprising:
 receiving, via the user interface, physiological goals of the subject;
 determining the light control plan for the subject based on the physiological goals of the subject, the physiological data, environmental data, and time data;
 operating, using the one or more processors, the light control valve to reduce the blue light ambient radiation based on the light control plan; and
 generating, using the one or more radiation generators, the therapeutic light radiation based on the light control plan.

12. The method of claim 11, wherein the light therapy system further comprises one or more location sensors configured to generate output signals conveying location data corresponding to a geographic location of the subject, and wherein the step of determining the light control plan comprises determining the light control plan for the subject based on the physiological goals of the subject, the physiological data, the environmental data, the time data, and the location data.

13. The method of claim 12, further comprising generating output signals conveying the time data, the time data being associated with the output signals from the one or more physiological sensors, one or more environmental sensors, and the one or more location sensors.

14. The method of claim 13, further comprising:
 receiving updated physiological data and updated location data;
 determining one or more adjustments of the light control plan based on the updated physiological data and the updated location data; and
 adjusting the reducing of the blue light ambient radiation and/or the generating of the therapeutic light radiation based on the one or more adjustments of the light control plan.

15. The method of claim 12, wherein the light therapy system further comprises one or more automated window blinds configured to reduce ambient light, one or more light therapy devices configured to generate the therapeutic light radiation onto the eyes of the subject, and/or one or more environment color control lamps configured to implement light therapy based on the light control plan.

16. The method of claim 11, wherein the one or more physiological sensors comprise one or more of: a gyroscope, a first accelerometer, a camera, a PPG sensor, a pupilometry sensor, a HRV sensor, an ambient light sensor, a proximity sensor, and/or a temperature sensor, and wherein the one or more location sensors comprise one or more of: a second accelerometer, a magnetometer, and/or a Global Positioning System (GPS) sensor.

17. The method of claim 11, wherein the light control valve comprises an optical shield, and wherein the therapeutic light radiation comprises at least blue light radiation, and wherein the one or more radiation generators is/are configured to emit generated radiation corresponding to at least blue light radiation in the melanopsin band of light spectrum.

18. The method of claim 11, wherein the therapeutic light radiation comprises wavelengths shorter than blue light radiation.

19. The method of claim 11, wherein the light control plan comprises one or more instructions corresponding to specific characteristics and timing of light radiation the subject experiences during the course of one or more days, the specific characteristics and timing comprising one or more of intensity level, wavelength, and/or duration.

20. The method of claim 11, wherein the physiological goals of the subject comprise adapting to shift-work, reducing the effect of jet lag, maximizing drug efficacy, re-aligning a circadian phase to meet a desired sleep/wake schedule, and/or reducing the symptoms of psychological disease or syndromes, and wherein the physiological data of the subject comprise fatigue levels, alertness levels, and/or an estimated circadian phase of the subject.

21. A device configured to control light exposure for circadian phase management and/or light deficient disorders of a subject, the device comprising:
 a user interface;
 means for receiving, via the user interface, a number of physiological goals of the subject and for generating a number of output signals conveying physiological data of the subject;
 radiation generation means configured to generate therapeutic light radiation onto the eyes of the subject; and
 means for determining a light control plan for the subject based on the number of physiological goals of the subject, the physiological data, environmental data, and time data;
 light control means for operating to reduce blue light ambient radiation reaching the eyes of the subject and based on the light control plan;
 processing means in communication with the user interface, the means for receiving, the light control means, and the radiation generation means;
 the light control means comprising at least one of a controlled optical lens means comprising at least one of a number of optical lenses controlled by the processing means to reduce the blue light ambient radiation based at least in part upon the light control plan and a commanded driver means comprising at least one of a hardware driver and a software driver configured to receive a command based at least in part upon the light control plan from the processing means and actuate the light control means in accordance with the command; and means for generating therapeutic light radiation based on the light control plan.

22. The device of claim 21 further comprising:
means for generating output signals conveying location data corresponding to a geographic location of the subject, wherein the step of determining the light control plan comprises determining the light control plan for the subject based on the physiological goals of the subject, the physiological data, the environmental data, the time data, and the location data.

23. The device of claim 22, further comprising means for generating output signals conveying the time data, the time data being associated with the physiological data, the environmental data, and the location data.

24. The device of claim 21, further comprising:
means for receiving updated physiological data, updated environmental data, and updated location data;
means for determining one or more adjustments of the light control plan based on the updated physiological data, the updated environmental data, and the updated location data; and
means for adjusting the reducing of the blue light ambient radiation and/or the generating of the therapeutic radiation based on the one or more adjustments of the light control plan.

* * * * *